United States Patent
Krafthefer

(10) Patent No.: US 7,900,500 B2
(45) Date of Patent: Mar. 8, 2011

(54) PARTICULATE MATTER SENSOR ELECTRODES WITH EMBEDDED SELF-CALIBRATOR, AND METHODS USING SAME

(75) Inventor: Brian C. Krafthefer, Stillwater, MN (US)

(73) Assignee: Honeywell International Inc., Morristown, NJ (US)

( * ) Notice: Subject to any disclaimer, the term of this patent is extended or adjusted under 35 U.S.C. 154(b) by 685 days.

(21) Appl. No.: 11/935,312

(22) Filed: Nov. 5, 2007

(65) Prior Publication Data

US 2009/0113983 A1   May 7, 2009

(51) Int. Cl.
*G01N 37/00* (2006.01)
(52) U.S. Cl. .......................................... 73/28.01
(58) Field of Classification Search .................. 73/28.01
See application file for complete search history.

(56) References Cited

U.S. PATENT DOCUMENTS

| | | | |
|---|---|---|---|
| 7,275,415 B2 * | 10/2007 | Rhodes et al. | 73/28.01 |
| 7,549,317 B2 * | 6/2009 | Rhodes et al. | 73/23.31 |
| 7,628,007 B2 * | 12/2009 | Kittelson et al. | 60/277 |

* cited by examiner

Primary Examiner — Hezron Williams
Assistant Examiner — Rodney T Frank
(74) Attorney, Agent, or Firm — Schwegman, Lundberg & Woessner P.A.

(57) ABSTRACT

A particulate matter (PM) sensor includes an embedded self-calibrator. The PM sensor is to be installed in an exhaust corridor of an internal combustion engine. The PM sensor can self-calibrate by imposing a known potential across a protective housing in which the conductive probe is suspended. An image charge that is imposed upon the conductive probe is fed back and correlated to generate an updated calibration for the PM sensor.

19 Claims, 6 Drawing Sheets

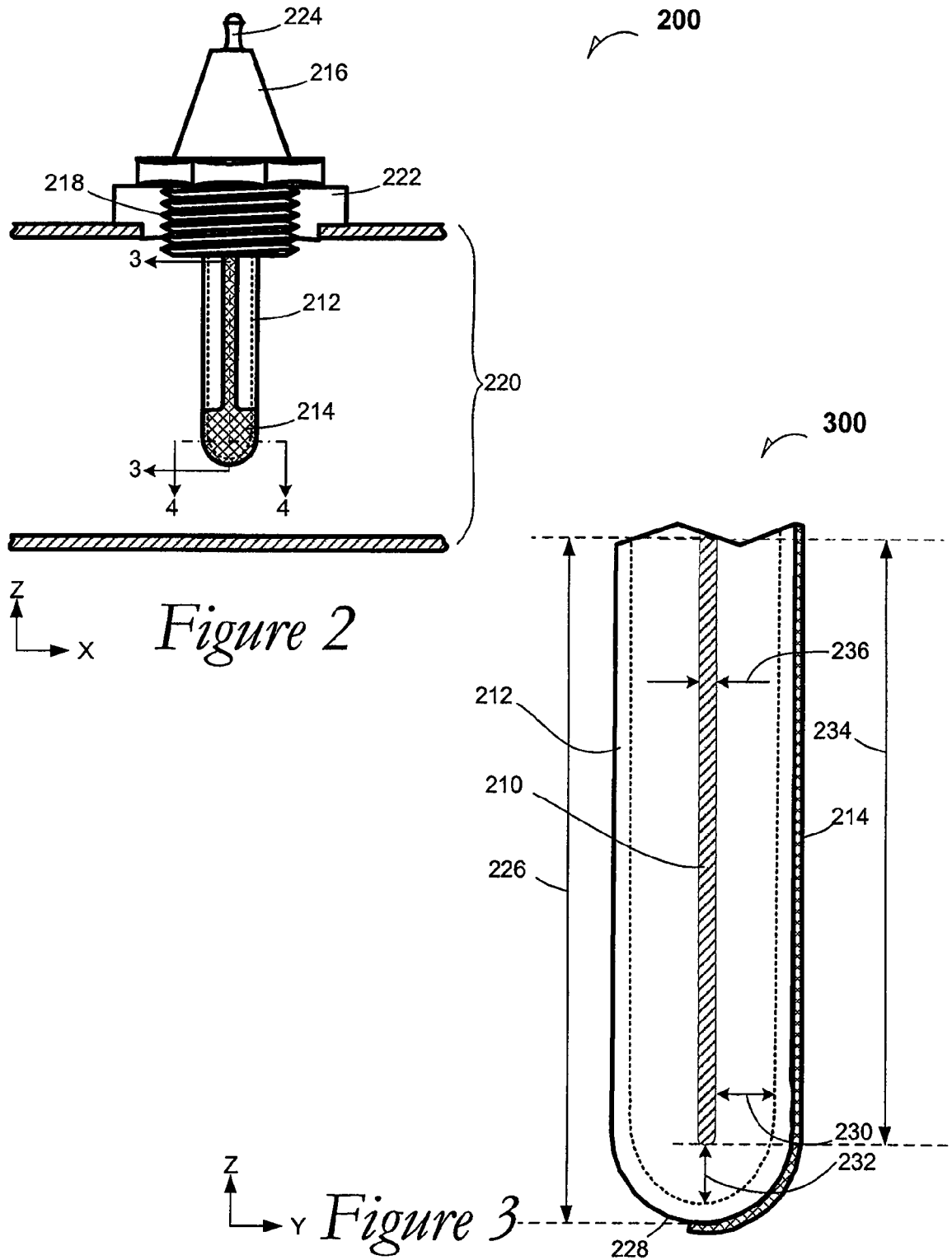

US 7,900,500 B2

PARTICULATE MATTER SENSOR ELECTRODES WITH EMBEDDED SELF-CALIBRATOR, AND METHODS USING SAME

TECHNICAL FIELD

Particulate matter (PM) sensors are used in internal combustion engines to determine combustion characteristics, particularly with respect to soot that results from incomplete combustion.

BRIEF DESCRIPTION OF THE FIGURES

Embodiments of this disclosure are illustrated by way of example and not limitation in the Figures of the accompanying drawings in which:

FIG. 2 is an elevational cross section of a particulate matter sensor with an embedded calibration electrode according to an embodiment;

FIG. 3 is a side cross section elevation of a particulate matter sensor with an embedded calibration electrode according to an embodiment;

DETAILED DESCRIPTION

A particulate matter (PM) sensor includes an embedded recalibration capability that may be used during real-time operation of the system that the PM sensor is monitoring. For example, a diesel engine may be operating and a periodic recalibration carried out irrespective of the fact that the diesel engine is being used. Consequently, the PM sensor has a self-calibration capability that is not subject to periodic or even unplanned downtime of the system.

The self-calibration of the PM sensor is carried out by imposing a known electrical potential between a calibration electrode and the sensor probe. The sensor probe measures the actual electrical potential that is experienced, and a comparator informs the system of the difference between the known potential and the actual potential that is experienced. By this method, the sensitivity of the PM sensor is known and deviations from previous known sensitivities that are caused by conditions such as sensor fouling, sensor breakdown, and others are noted. Consequently, the PM sensor can be recalibrated in situ.

Figure 1:
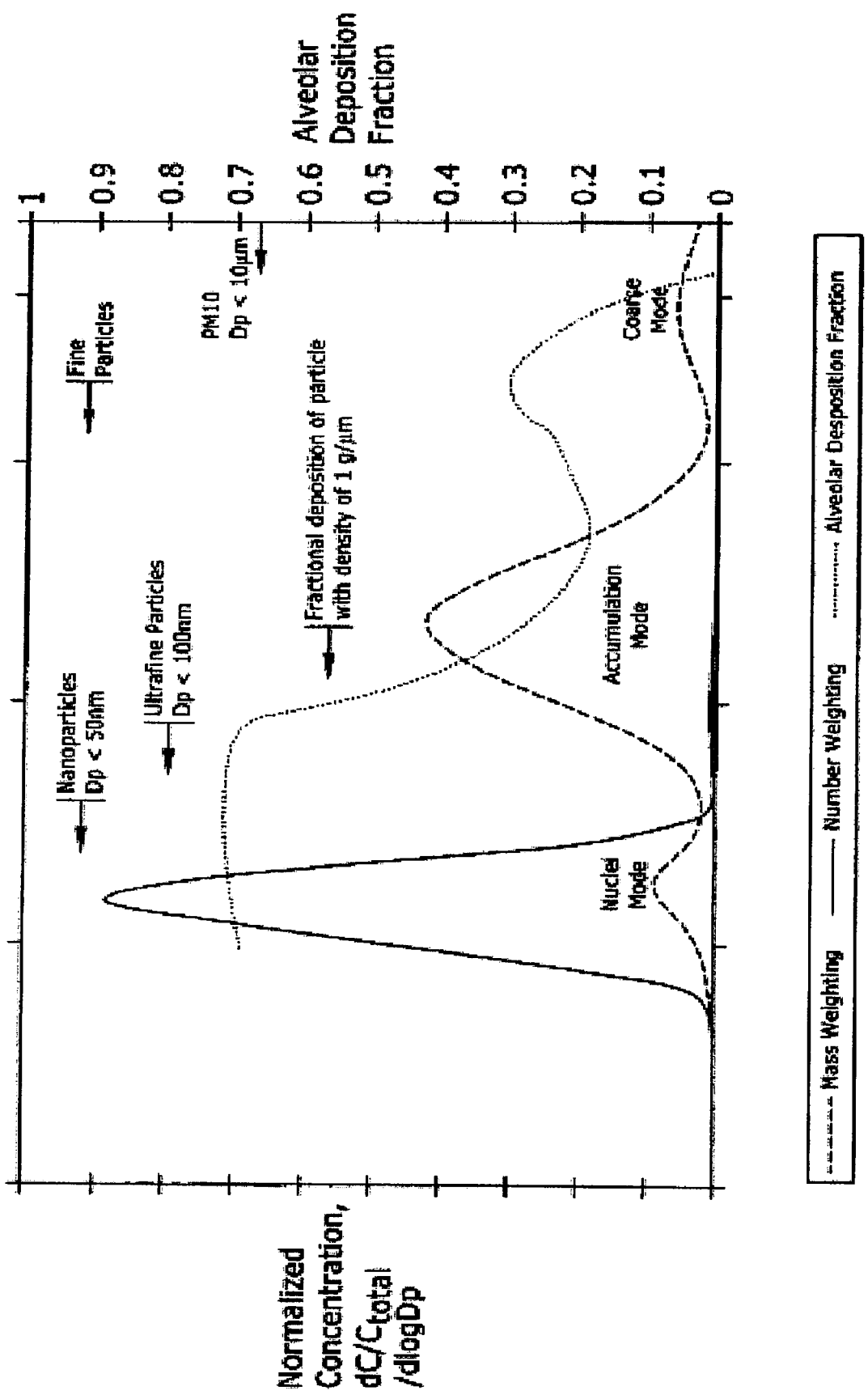
FIG. 1 is a graph showing engine exhaust mass and number weighted size distributions.

FIG. 1 is a graph showing engine exhaust and a number of weighted size distributions shown. The graph illustrates a diesel particulate matter (PM) number and mass weighted distribution. The PM follows a lognormal, trimodal size distribution with the concentration in any size range being proportional to the area under the corresponding curve in that range. The nuclei mode particles range in diameter from 0.005 to 0.05 micron (5-50 nm). They may consist of metallic compounds, elemental carbon, and semivolatile organic and sulfur compounds that form particles during exhaust dilution and cooling. The nuclei mode typically contains 1 to 20 percent of the particle mass and more than 90 percent of the particle number. The accumulation mode particles range in diameter from 0.05 to 0.5 micron (50 to 500 nm). Most of the mass, composed primarily of carbonaceous agglomerates and adsorbed materials, is found here. The coarse mode consists of particles larger than one micron in diameter and contains 5 to 20 percent of the PM mass. These relatively large particles are formed by re-entrainment of particulate matter, which has been deposited on cylinder and exhaust system surfaces.

Particles in the nuclei mode and in the accumulation mode appear to be formed by different mechanisms. Accumulation mode particles are primarily carbonaceous and are associated with rich combustion and poor subsequent oxidation during the engine cycle. On the other hand, most nuclei mode particles are not even formed until the exhaust combustion products dilute and cool. The nuclei mode particles consist of a complex mix of sulfuric acid and partially combusted fuel and lubricating oil. Formation of these two types of particles likely occurs under different engine operating conditions. One condition is heavy loads favoring carbonaceous accumulation mode particles. Another condition is light loads most likely favoring the formation of vapor phase precursors of nuclei mode particles. The precursors may not undergo gas-to-particle conversion until the exhaust cools and dilutes in the atmosphere.

In order to meet various and changing emission standards, diesel engines need to be fitted with combustion control systems. Also, an after treatment system including particle filters or traps will be needed. To make such combustion control systems and after treatment devices reasonably feasible to reduce particulate emissions from an engine, an effective exhaust particulate sensor is needed. Particulate traps are available but they are large, expensive and significantly reduce fuel economy. The reduction in fuel economy is due to additional back pressure in the exhaust system being applied to the engine.

FIG. 2 is an elevational cross section of a PM sensor 200 with an embedded calibration electrode according to an embodiment. The PM sensor 200 includes a probe 210 (FIG. 3), also referred to as a sensor probe, that is suspended within a protective housing 212. In an embodiment, the protective housing 212 is a high-temperature sound dielectric such as alumina. Other materials such as thoria or hafnia may be selected. Other materials such as ceria, yttria or ytterbia may be selected. In an embodiment, the protective housing 212 is formed by plasma spraying the selected material onto a mandrel, followed by removing the mandrel.

A calibration electrode 214 is disposed on the exterior of the protective housing 212. The calibration electrode 214 may also be referred to as an embedded self-calibrator. In an embodiment, the calibration electrode 214 is a metal that may withstand extreme conditions, such as elevated-temperature, turbulent exhaust-gas flow regimes. In an embodiment, the calibration electrode 214 is formed upon the protective housing 212 by sputter coating a patterned titanium nitride film onto the protective housing 212. In an embodiment, the calibration electrode 214 is formed upon the protective housing 212 by sputter coating a patterned iron-aluminum intermetallic alloy film onto the protective housing 212.

The PM sensor 200 also includes a sensor housing 216 that is physically coupled to the probe 210. The coupling may be through an externally threaded fitting 218. The externally threaded fitting 218 may couple to an exhaust corridor 220 such as an exhaust pipe or an exhaust manifold. A sensor mounting 222 is provided that may be welded to the exhaust corridor 220 such as with an internally threaded orifice that accepts the externally threaded fitting 218.

The PM sensor 200 communicates to the external world through a signal coupling 224. In an embodiment, a spark plug chassis may be redesigned to accept the probe 210 and the protective housing 212 with the calibration electrode 214. The signal coupling 224 may have the capability to accept significant electrical potentials to calibrate the probe 210, as well as to transceive sensitive signals to accomplish calibration and recalibration of the probe 210.

FIG. 3 is a cross-section elevation 300 of a portion of the PM sensor 200 depicted in FIG. 2. The view of the PM sensor 200 is taken along the section line 3-3 from FIG. 2. The PM sensor 200 has been rotated 90° such that the probe 210 is revealed. In an embodiment, the probe 210 is made of a stainless steel. In an embodiment, the probe 210 is made of Kovar®, which can be a nickel-ferrous cobalt alloy made by Carpenter Technology Corporation of Wyomissing, Pa. Other metals may be used based upon a given application.

Further, it is seen that the calibration electrode 214 extends along the length 226 of the protective housing 212. It can also be seen that the calibration electrode 214 may wrap around the distal end 228 of the protective housing 212. In an embodiment the lateral distance 230 between any portion of the length of the calibration electrode 214 and the probe 210 is the same as the distal distance 232 between the tip of the probe 210 and the calibration electrode 214 at the distal end 228 of the protective housing 212.

The probe 210 may have various dimensions. In an embodiment, the probe 210 may have a length 234 between about 0.25 inches and about 12 inches. In an embodiment, the probe 210 may have a length 234 in a range from about 3 inches to about 4 inches. The probe 210 may also have a thickness 236 between about $1/32$ inches and about $3/8$ inches. In an embodiment the thickness 236 of the probe 210 is about $1/8$ inch.

Figure 4:
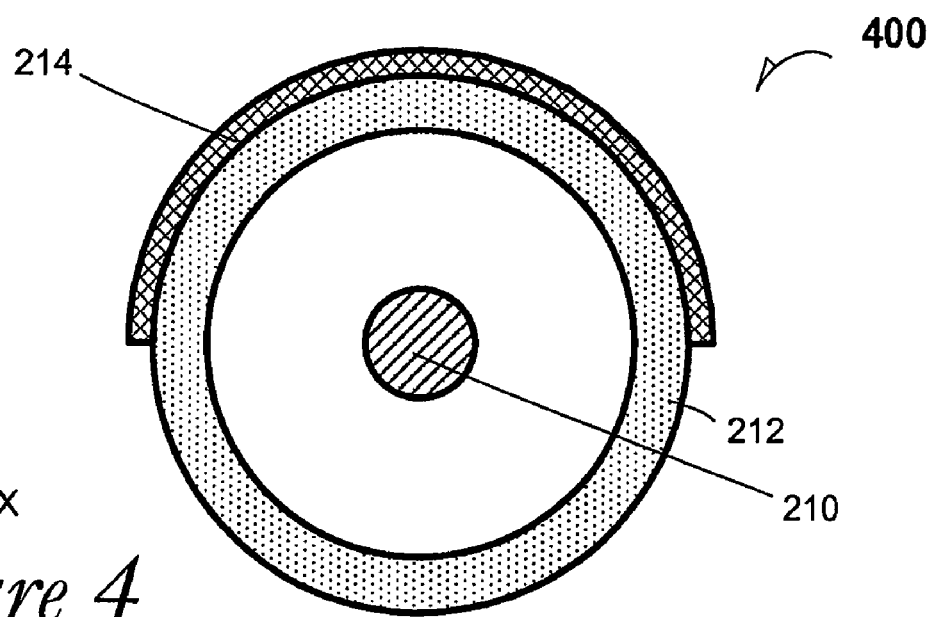
FIG. 4 is a detail cross section of a portion of the particulate matter sensor depicted in FIG. 2 with an embedded calibration electrode according to an embodiment.

FIG. 4 is a cross-section 400 of a portion of the PM sensor 200 depicted in FIG. 2. The view of the PM sensor 200 is taken along the section line 4-4 from FIG. 2. The probe 210 is depicted suspended within the protective housing 212, and the calibration electrode 214 is depicted disposed upon the outer surface of the protective housing 212.

Figure 5:
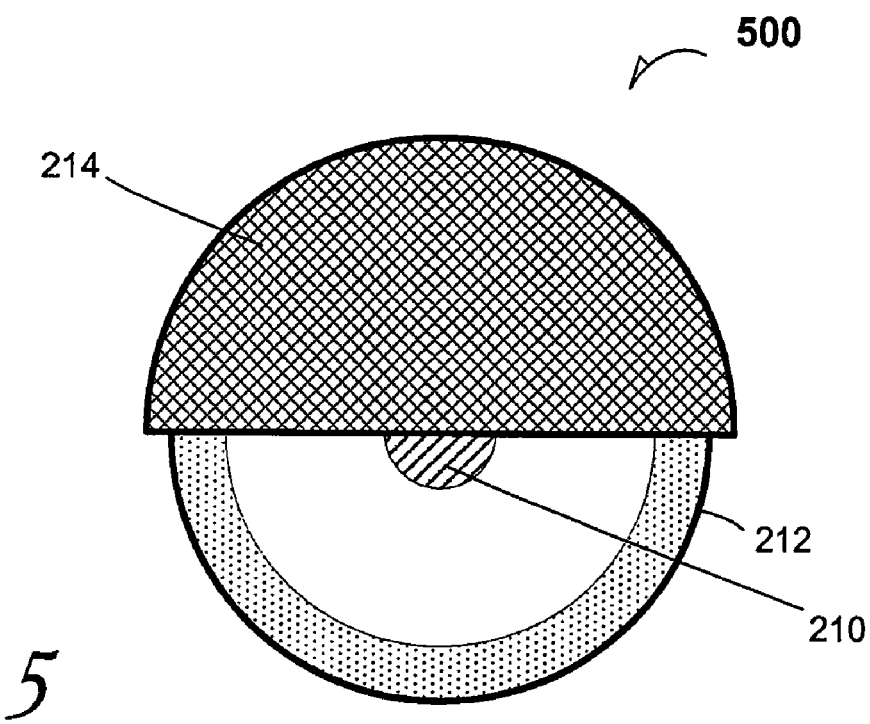
FIG. 5 is a bottom plan of the particulate matter sensor depicted in FIG. 2 with an embedded calibration electrode according to an embodiment.

FIG. 5 is a bottom plan 500 of a portion of the PM sensor 200 depicted in FIG. 2. The probe 210 is depicted suspended within the protective housing 212, and the calibration electrode 214 is depicted disposed upon the outer surface of the protective housing 212 at the distal end 228 (FIG. 3) of the protective housing. In an embodiment, the calibration electrode 214 covers half of the distal end 228 of the protective housing 212. In an embodiment, the calibration electrode 214 covers some, but less than half of the distal end 228 of the protective housing 212. In an embodiment, the calibration electrode 214 covers more than half but not all of the distal end 228 of the protective housing 212.

Figure 6:
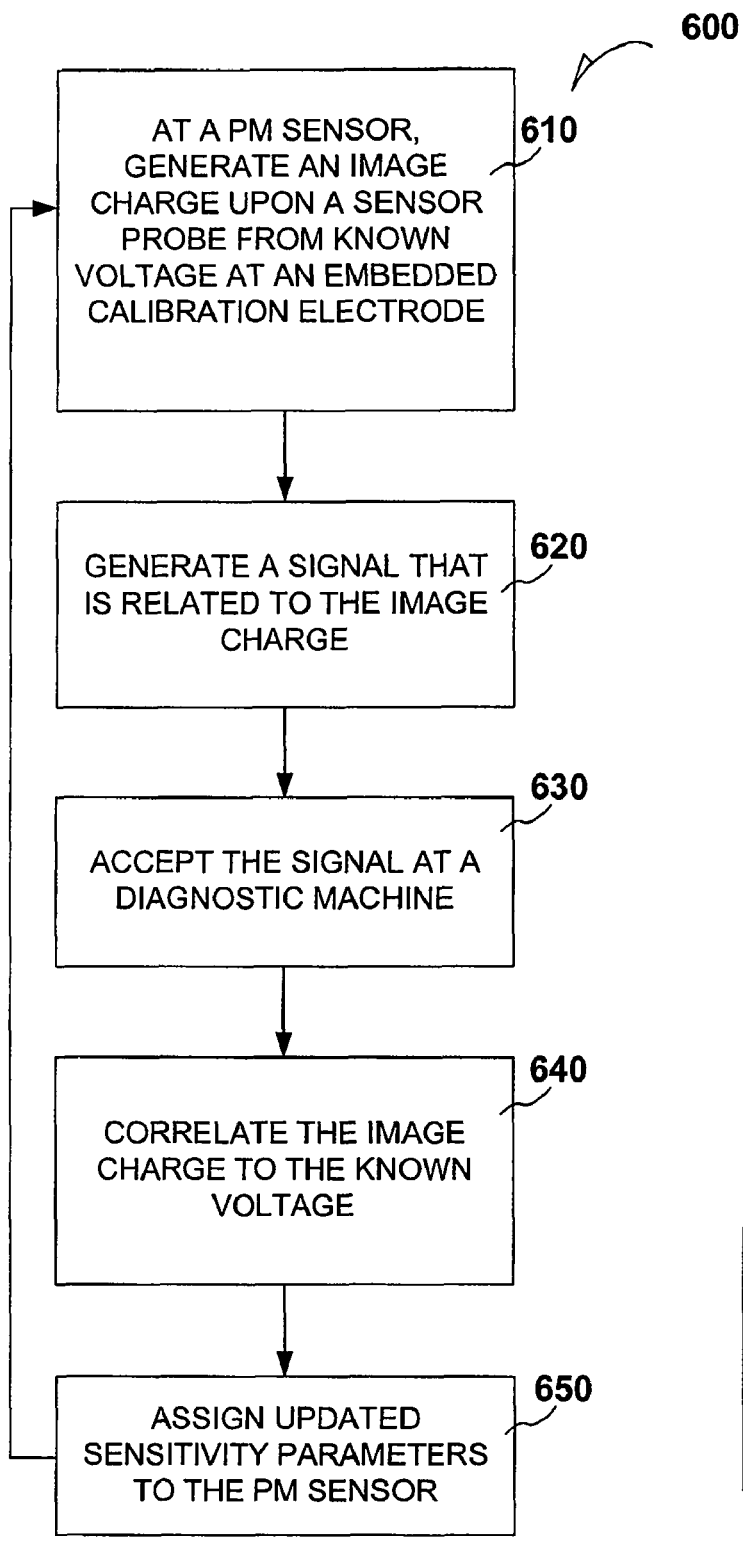
FIG. 6 is a method flow diagram for recalibrating a particulate matter sensor according to an embodiment.

FIG. 6 is a flow diagram of a method 600 of calibrating and recalibrating a PM probe for a particulate matter sensor according to an embodiment. At 610, the method includes generating a known voltage at the calibration electrode, such as the calibration electrode 214 depicted in the previous FIGS. The known voltage creates an electrical field that reaches across the protective housing 212 and is applied to the sensor probe 210. The result is the generation of an image charge as sensed on the sensor probe 210. An image charge is generated by charges on the diesel particles in the exhaust and the signal seen is due to separation of these charges in the exhaust stream. The image charge is correlated to the PM mass. Further, the image charge is the first part of a feedback signal that is generated for correlating the known potential to the actual potential that was detected at the sensor probe 210.

At 620, the method includes generating a signal that is related to the image charge generated at the sensor probe 210. Consequently, the second part of a feedback signal is the generating of the signal. In an embodiment, the method commences at 610 and terminates at 620.

At 630, the method includes accepting the signal at a diagnostic machine. The third part of generating a feedback signal and correlating the signal to the known potential occurs at 630. The diagnostic machine may be a processor or a specialized device.

At 640, the method includes comparing the known voltage that was applied across the protective housing and the sensor probe, and the actual voltage experienced in real time at the sensor probe. The fourth part of generating a feedback signal and correlating the signal to the known potential occurs at 640. In a non-limiting example, the known voltage that was applied across the calibration electrode 214 and the sensor probe 210 is compared to the actual voltage experienced in real time at the sensor probe 210.

At 650, the method includes assigning updated sensitivity parameters to the PM sensor based upon the difference between the known voltage and the actual voltage. In a non-limiting example embodiment, the PM sensor 200 is calibrated during a steady-state operation of a combustion engine such as a diesel engine. A known potential is imposed across the calibration electrode 214 and the sensor probe 210. An image charge is sensed and a signal is fed back to a diagnostic machine. The signal is compared to the known potential that was imposed, and the sensitivity of the sensor probe 210 is updated.

According to a method embodiment, the updating is done based upon a defined interval. For a given internal combustion engine, the defined interval may be upon startup of the internal combustion engine. In an embodiment, the defined interval may be after a given number of service hours of the internal combustion engine, such as every 100 hours, every 500 hours, every 1,000 hours, etc. The defined interval, when it is selected in hours, may be related to known periodic maintenance intervals.

According to a method embodiment, the updating is done based upon a detected diagnostic deviation of the internal combustion engine. For example, the PM sensor itself may be detecting particulates outside a selected concentration range, and the methods of imposing, generating, comparing, and updating may be carried out to determine if the PM sensor has deviated from the previous calibration. In another example, a different system in the internal combustion engine may be deviating from known performance parameters, and the methods of imposing, generating, comparing, and updating may be carried out to determine whether the deviation may be due to a changed sensor probe.

Figure 7:
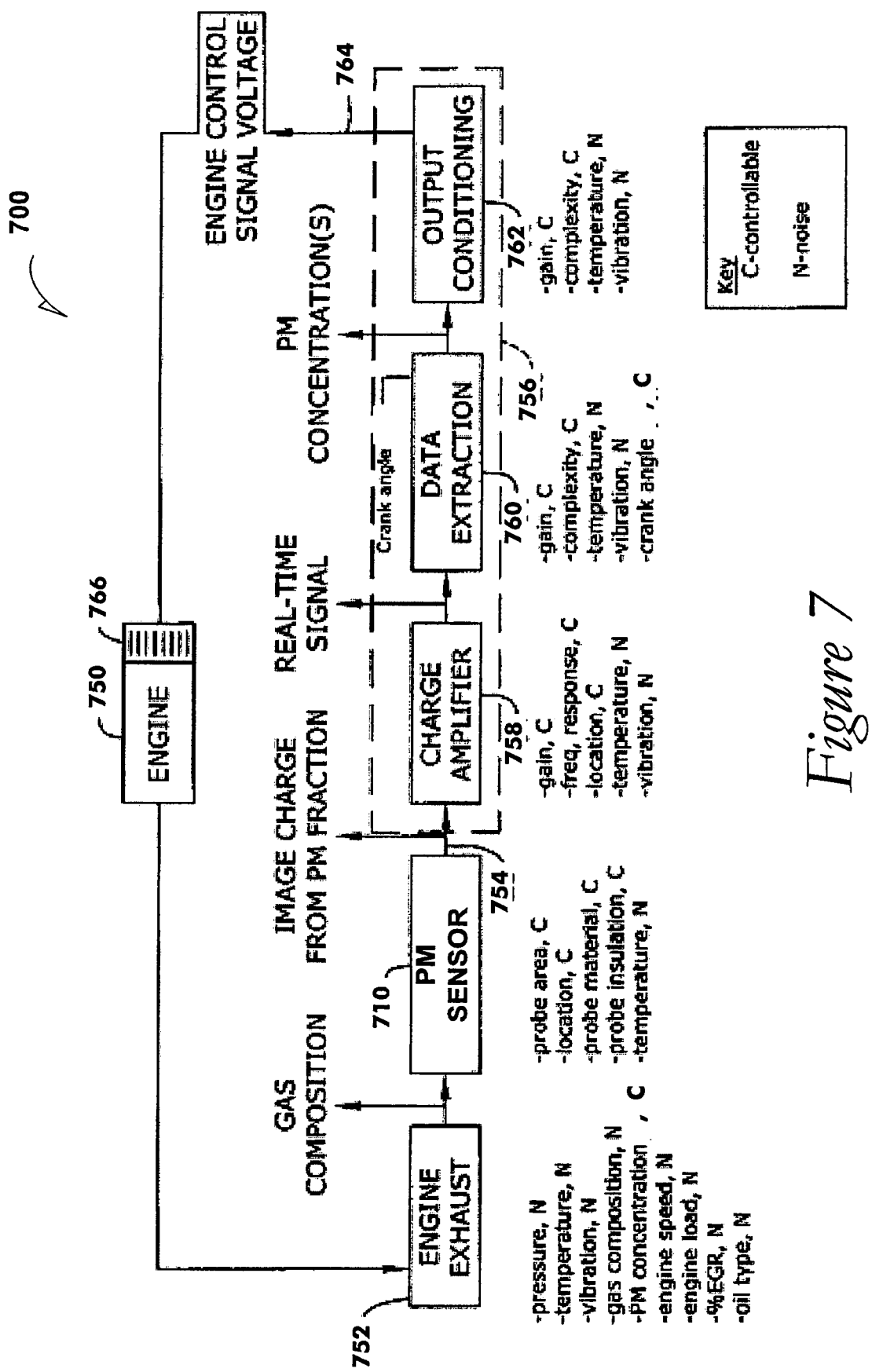
FIG. 7 is a block diagram of a loop for engine control based on parameters of an engine, including the particulate matter of its exhaust emissions as determined by a particulate matter sensor with an embedded calibration electrode according to an embodiment.

FIG. 7 is a block diagram of one version of a loop 700 for engine control based on the PM of exhaust emissions. An engine 750 may output engine exhaust 752, which is sensed by a PM sensor 710, which in turn may output an image charge signal 754 to a processor 756. The processor 756 may include a charge amplifier 758, a data extractor 760, and an output signal conditioner 762, among other components.

The image charge signal 754 may go to the charge amplifier 758, which may output a real-time signal to the data extractor 760, which may receive a crankshaft angle determination. Other parameter inputs may be received and evaluated for improving engine control and performance. The output from the data extractor 760 may include an electronic indication of the PM concentration of a given sensor. This electronic indication may go to the output signal conditioner 762, which indication may be correlated with other various inputs of engine data. Examples of various inputs include timing, temperature, percent exhaust-gas recirculation (EGR), valve position, and others. These several inputs may provide engine control signal voltage 764 to the fuel injection and manifold system 766 of the engine 750 in order to control both PM emissions and the in situ recalibration of the PM sensor 710.

It can now be appreciated that several complex combinations of engine performance can be monitored in part by use of a PM sensor embodiment set forth in this disclosure. Consequently, the method of recalibrating the PM sensor during operation of the engine provides real-time adjustment of the entire system, such that a degraded PM sensor will not necessarily be detrimental to achieving a selected PM emissions level.

Figure 8:
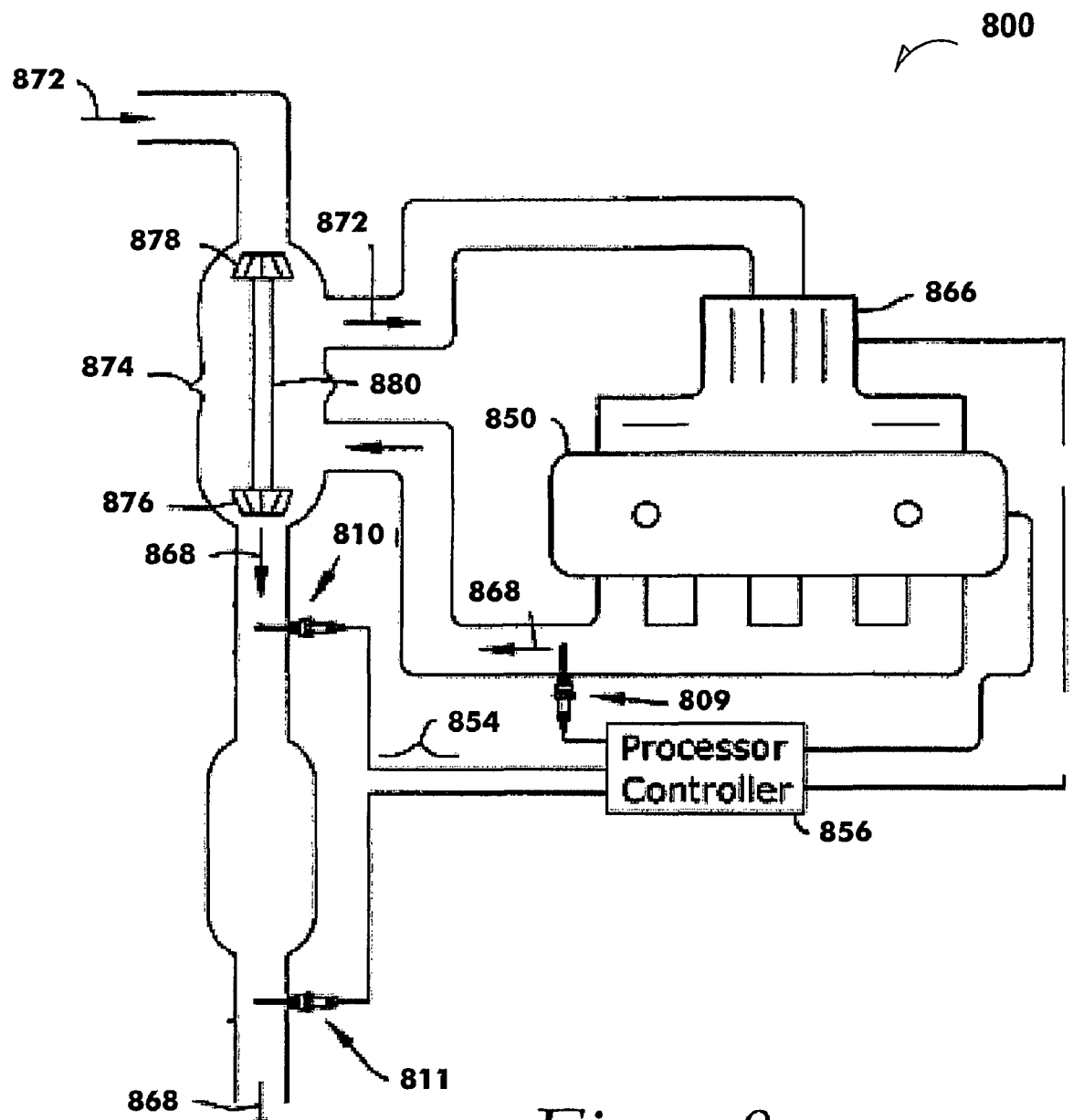
FIG. 8 is a schematic diagram of an engine system that uses an in situ recalibration for a particulate matter sensor according to an embodiment.

FIG. 8 is a schematic diagram of an engine system 800 that uses a PM sensor according to an embodiment. A PM sensor 810, that includes a self-calibrator such as a calibration electrode embodiment disclosed herein, generates a signal 854 to indicate an amount of particulate matter in the exhaust 868. The signal 854 may be conveyed to a processor 856 (or a specialized controller 856). The processor 856 may be connected to other particulate sensors 809 and 811, engine sensors, and a fuel injection and intake manifold system 866. Based on signals 854 from one or more of the PM sensors 810, the PM sensors 809 and 811, and sensors in fuel injection and intake manifold system 866, the engine 850 may be controlled based upon several engine parameters. Non-limiting examples include fuel flow, EGR, injection timing, needle lift, crankshaft angle, cylinder pressure, valve position and lift, manifold vacuum, fuel/air mixture, and the intake properties of air 872. The processor 856 may provide control information signals 854 or other information from or about the engine 850, to regulate the fuel injection amount and timing, EGR percent, valve control, and intake manifold system 866, and the like to cause the engine 850 to expel a reduced amount of particulate emissions. The exhaust 868 may enter a turbocharger 874 and cause a turbine 876 to spin and turn a compressor 878 via a shaft 880. The exhaust corridor may also include a muffler 875.

In an example embodiment, the PM sensor 810 is pre-calibrated and operated for an initial time period. Next, the PM sensor 810 is recalibrated at ordinary operating temperatures for a diesel engine. The temperature is about 670° C. and a resulting Bosch smoke number of exhaust 868 is at least 5. This number may correspond to a particle mass concentration of approximately 350 mg/m$^3$.

The PM sensor 810 is recalibrated by imposing a known potential upon the sensor probe by generating a voltage at the calibration electrode. The actual potential is conveyed back to the processor 856, and the updated sensitivity of the PM sensor 810 is recorded. In an embodiment, the PM sensor 810 puts out a reproducible rms signal representing its image charge monitoring of the exhaust 868, which is correlated to exhaust smoke as characterized by the Bosch smoke number.

Figure 9:
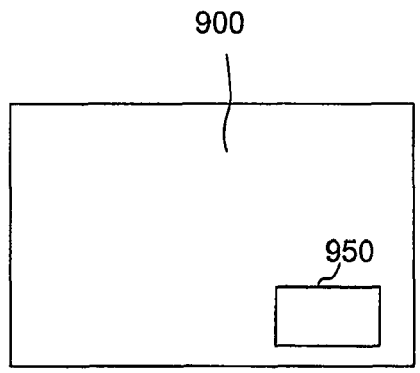
FIG. 9 is a schematic diagram illustrating a medium having an instruction set, according to an example embodiment.

FIG. 9 is a schematic diagram illustrating a medium having an instruction set, according to an example embodiment. A machine-readable medium 900 includes any type of medium such as a link to the internet or other network, a disk drive or solid state memory device, or the like. A machine-readable medium 900 includes instructions within an instruction set 950. The instructions, when executed by a machine such as an information handling system or a processor, cause the machine to perform operations that include recalibration method embodiments.

In an example embodiment, machine-readable medium 900 includes an instruction set 950, that when executed by a machine, causes the machine to perform operations including in situ recalibration of a PM sensor. In an embodiment, the machine-readable medium 900 and instruction set 950 are disposed in the medium 900 and are locatable within the engine compartment of an internal combustion engine such as in a diesel tractor. In an embodiment, the machine-readable medium 900 and instruction set 950 are disposed in the medium 900 and are locatable within the cab such as near the firewall of the engine compartment of an internal combustion engine such as in a diesel tractor.

Thus, a system, method, and machine-readable medium including instructions for Input/Output scheduling have been described. Although the various calibration, in situ recalibration, and methods have been described with reference to specific example embodiments, it will be evident that various modifications and changes may be made to these embodiments without departing from the broader scope of the disclosed subject matter. Accordingly, the specification and drawings are to be regarded in an illustrative rather than a restrictive sense.

What is claimed is:

1. A method comprising:
    imposing an image charge with a known electrical potential from a calibration electrode upon a sensor probe of a particulate material (PM) sensor that is installed in an internal combustion engine exhaust corridor; and
    generating a feedback signal based upon the image charge.

2. The method of claim 1, further including:
    receiving a diagnostic feedback signal from the PM sensor, wherein the diagnostic feedback signal is proportional to the image charge;
    comparing the diagnostic feedback signal to the known electrical potential; and
    updating a sensitivity parameter for the PM sensor.

3. The method of claim 1, wherein imposing the image charge includes imposing the image charge across a protective housing in which the sensor probe is suspended, by generating a known potential from the calibration electrode that is disposed upon and exterior to the protective housing.

4. The method of claim 1, wherein imposing the image charge includes imposing the image charge across a protective housing in which the sensor probe is suspended, by generating a known potential from the calibration electrode that is disposed upon and exterior to the protective housing, the method further including:
    receiving a diagnostic feedback signal from the PM sensor, wherein the diagnostic feedback signal is proportional to the image charge;
    comparing the diagnostic feedback signal to the known electrical potential; and
    updating a sensitivity parameter for the PM sensor.

5. The method of claim 1, wherein imposing the image charge includes imposing the image charge across a protective housing in which the sensor probe is suspended, by generating a known potential from the calibration electrode that is disposed upon and exterior to the protective housing, the method further including:

receiving a diagnostic feedback signal from the PM sensor, wherein the diagnostic feedback signal is proportional to the image charge;
comparing the diagnostic feedback signal to the known electrical potential;
updating a sensitivity parameter for the PM sensor; and
repeating the imposing, generating, comparing, and updating.

6. The method of claim 5, wherein repeating the imposing, generating, comparing, and updating is carried out during defined intervals.

7. The method of claim 5, wherein repeating the imposing, generating, comparing, and updating is carried out upon detection of a diagnostic deviation.

8. A method, comprising:
imposing an image charge from a known electrical potential upon a sensor probe of a particulate matter (PM) sensor that is installed in an internal combustion engine, wherein the PM sensor includes:
  a protective housing coupled to a sensor housing;
  a signal coupling coupled to the sensor housing;
  a sensor probe suspended within the protective housing; and
  a calibration electrode disposed exterior to and on a surface of the protective housing, wherein imposing the image charge is accomplished by the calibration electrode generating the known electrical potential, the method further including:
generating a signal that is related to the image charge;
accepting the signal at a diagnostic machine;
comparing the known voltage to an actual voltage related to the image charge; and
updating a sensitivity parameter for the sensor probe.

9. The method of claim 8, following the updating, the method further including repeating the imposing, generating, comparing, and updating, and wherein repeating the imposing, generating, comparing, and updating is carried out either during defined intervals or upon detection of a diagnostic deviation.

10. A particulate matter (PM) sensor comprising:
a protective housing;
a sensor probe suspended within the protective housing; and
a calibration electrode disposed exterior and on the surface of the protective housing, wherein the calibration electrode includes a first form factor that is elongated near the sensor probe length, and a second form factor disposed at the protective housing distal end.

11. The PM sensor of claim 10, further including a diagnostic machine coupled to the PM sensor, wherein the diagnostic machine includes capability to generate a known potential at the calibration electrode, to receive a signal from the sensor probe, to compare the signal to the known potential, and to update sensitivity parameters for the sensor probe.

12. The PM sensor of claim 10, further including:
a diagnostic machine coupled to the PM sensor, wherein the diagnostic machine includes capability to generate a known potential at the calibration electrode, to receive a signal from the sensor probe, to compare the signal to the known potential, and to update sensitivity parameters for the sensor probe; and
a machine-readable medium that contains instructions to carry out a method of imposing an image charge with a known electrical potential upon the sensor probe, and generating a feedback signal based upon the image charge.

13. The PM sensor of claim 12, wherein the machine-readable medium is couplable to an internal combustion engine.

14. The PM sensor of claim 10, wherein the protective housing is a dielectric material.

15. The PM sensor of claim 10, wherein the protective housing is a dielectric material selected from ceria, thoria, hafnia, yttria, ytterbia, and combinations thereof.

16. The PM sensor of claim 10, wherein the calibration electrode at the distal end of the protective housing covers half of the distal end thereof.

17. The PM sensor of claim 10, wherein the calibration electrode at the distal end of the protective housing covers some, but less than half of the distal end thereof.

18. The PM sensor of claim 10, wherein the calibration electrode at the distal end of the protective housing covers more than half but not all of the distal end thereof.

19. The PM sensor of claim 10, further including a machine-readable medium that contains instructions to carry out a method of imposing an image charge with a known electrical potential upon the sensor probe, generating a feedback signal based upon the image charge, and wherein the machine-readable medium is couplable to an internal combustion engine.

\* \* \* \* \*